(12) United States Patent
Chao

(10) Patent No.: US 7,399,288 B2
(45) Date of Patent: Jul. 15, 2008

(54) ADJUSTABLE NECK BRACE

(76) Inventor: Richard Chao, 4F, No.35-3, Lane165, Sec.1, Xinsheng S. Rd., Taipei City (TW)

( * ) Notice: Subject to any disclaimer, the term of this patent is extended or adjusted under 35 U.S.C. 154(b) by 228 days.

(21) Appl. No.: 11/437,738

(22) Filed: May 22, 2006

(65) Prior Publication Data

US 2007/0270728 A1    Nov. 22, 2007

(51) Int. Cl.
*A61F 5/00* (2006.01)
(52) U.S. Cl. .......................... 602/18; 602/36
(58) Field of Classification Search .................. 602/18, 602/17, 32, 61; 128/DIG. 23; 606/241, 237
See application file for complete search history.

(56) References Cited

U.S. PATENT DOCUMENTS

| | | | | |
|---|---|---|---|---|
| 2,102,069 A | * | 12/1937 | Hanicke | 602/18 |
| 3,776,224 A | * | 12/1973 | McFarland | 602/18 |
| 5,046,490 A | * | 9/1991 | Young et al. | 602/17 |
| 5,688,229 A | * | 11/1997 | Bauer | 602/18 |
| 6,726,643 B1 | * | 4/2004 | Martin | 602/18 |
| 2004/0204666 A1 | * | 10/2004 | Marsh | 602/18 |

* cited by examiner

*Primary Examiner*—Terrell Mckinnon
*Assistant Examiner*—James M Robinson
(74) *Attorney, Agent, or Firm*—Muncy, Geissler, Olds & Lowe, PLLC

(57) ABSTRACT

An adjustable neck brace worn at a human neck for fixing a cervical vertebra includes a cover panel and an adjusting device fixed onto a surface of the cover panel, and the adjusting device includes an adjusting rod, a limit member and an adjusting knob disposed on a surface corresponding to the adjusting rod, and an end of the limit member includes a bracket, and the adjusting knob links an adjusting gear installed at the adjusting rod, and an end of the adjusting rod includes a height adjusting plate having a supporting portion for supporting a chin. With the foregoing technical measures, the invention features a secured and stable structure to maximize the effects of medical treatment and physical therapy. The height of the supporting portion can be adjusted to provide users a feedback about a definite feel of the adjustment through the bracket.

10 Claims, 11 Drawing Sheets

ADJUSTABLE NECK BRACE

FIELD OF THE INVENTION

The present invention relates to an adjustable neck brace, and more particularly to an adjustable neck brace that has an adjusting device for flexibly adjusting the support height of the neck brace.

BACKGROUND OF THE INVENTION

Our neck provides a substantial support to our body and protects the upward and downward transmissions of our basic biological movement messages and nutrition. As our working pressure increases, the pace of our living becomes faster; as computer networks are well developed, neck diseases jeopardize our body and seriously affect our living and work. As indicated in researches, more than 70% of the people with an age of 60 or over has neck diseases or injuries to some extent, and the average age of these patients tends to be younger and younger.

For patients having a neck disease or patents still having a neck problem after performing surgical operations, a neck brace is usually worn on the patient's neck for neck tractions as disclosed in R.O.C. Pat. Publication No. 354254 entitled "Physical therapy device for herniated nucleus pulposus or sprain and injury" and U.S. Pat. No. 4,881,529. However, the foregoing traditional patented neck braces are fixed to a patient's neck and its height for supporting the neck cannot be adjusted flexibly. Since the diameter and length of each patient's neck vary, the neck brace must come with different sizes and specifications to meet the requirements of different patients, and thus causing tremendous inconvenience to manufactures for the production and inventory of the neck braces.

R.O.C. Pat. Publication No. M277433 entitled "Improved neck band" discloses a neck band to overcome the shortcomings of traditional neck bands that cannot flexibly adjust the supporting height. The improved neck band includes a height adjusting plate surrounded around a circular plate for adjusting the height of the neck band, and a lining pad is coupled separately on the internal sides of both circular plate and height adjusting plate, and the circular plate is worn around a patient's neck, characterized in that a half portion of the circular plate is provided for connecting the height adjusting plate, and the middle portion of the circular plate includes a groove and a plurality of limit protrusions and elastic latch points disposed evenly on both sides of the groove. Both sides of a propping portion at the middle of the height adjusting plate include a plurality of slide tracks corresponding to the limit protrusions and operating together with the elastic latch points of the circular plate, and a plurality of fixing holes disposed successively from top to bottom. With the foregoing structure, the height adjusting plate can be fixed onto the circular plate by connecting the slide tracks and the circular plate, and the height of the neck band can be adjusted by moving and changing the height of the slide track. However, such arrangement fixes the elastic latch points into the fixing holes, so that when a user wants to adjust the height of the height adjusting plate, the user has to remove the height adjusting plate from the circular plate and then latch the elastic latch points after a desired height is selected, so as to install the neck band onto the user's neck. Users have to repeat the operations for several times before the neck band is adjusted to an appropriate height, and thus making the use very inconvenient. Further, the design of the latch connection is not secured enough for the installation of the neck band onto a user's neck, and it is difficult to maximize the effects of the device of this sort.

SUMMARY OF THE INVENTION

The primary objective of the present invention is to overcome the foregoing shortcomings and avoid the existing deficiencies by providing an adjustable neck brace worn at a user's neck, and the height of a support portion can be adjusted flexibly by a simple operation to meet the requirements of different users.

To achieve the foregoing objective, the adjustable neck brace in accordance with the present invention comprises a cover panel and an adjusting device both installed on the surface of the cover panel. The adjusting device includes an adjusting rod, and a plurality of positioning grooves and a plurality of protrusions disposed separately on both sides of the adjusting rod. The surface of a casing includes a limit member and an adjusting knob, and the limit member includes a bracket corresponding to the positioning groove, and the adjusting knob includes an adjusting gear extended and coupled to the protrusion, a height adjusting plate coupled to the connecting portion, a supporting portion protruded from the height adjusting plate for supporting a user's chin, and a force is exerted on the adjusting knob to drive the adjusting rod to produce a displacement by the adjusting gear to lift the supporting portion to a desired height, and the bracket is latched into the positioning groove, and the adjusting rod forms a fixing relation to maintain the desired height. In addition to the secured and stable features, the present invention also allows users to know about the height adjustment by a clear sound and touch of the bracket while the height is being adjusted.

DETAILED DESCRIPTION OF THE PREFERRED EMBODIMENTS

The present invention will now be described in more detail hereinafter with reference to the accompanying drawings as follows:

To make it easier for our examiner to fully understand the objective of the invention, its structure, innovative features, and performance, we use a preferred embodiment together with the attached drawings for the detailed description of the invention.

Figure 1:
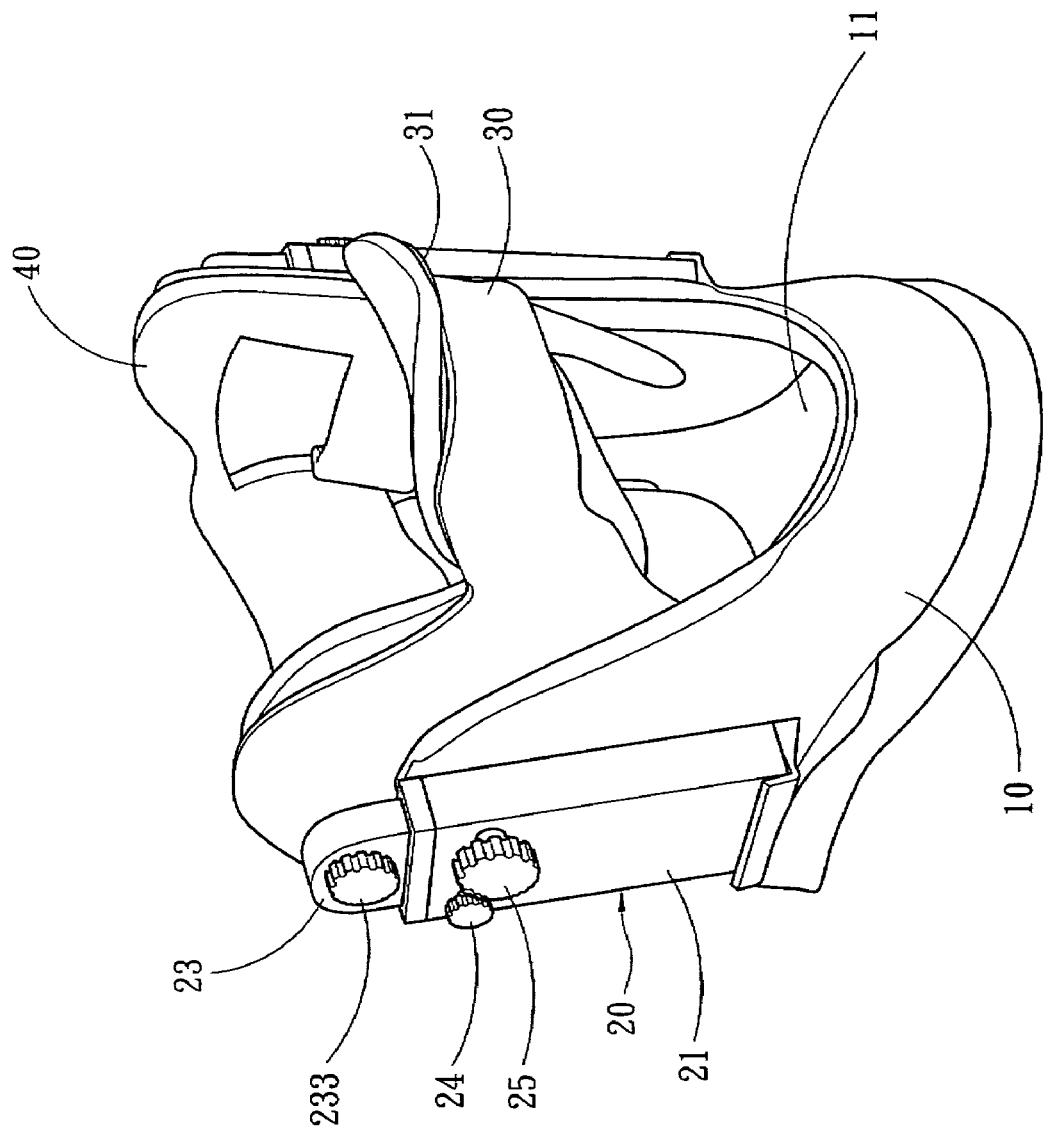
FIG. 1 is a perspective view of a structure of a preferred embodiment of the present invention.
Figure 2:
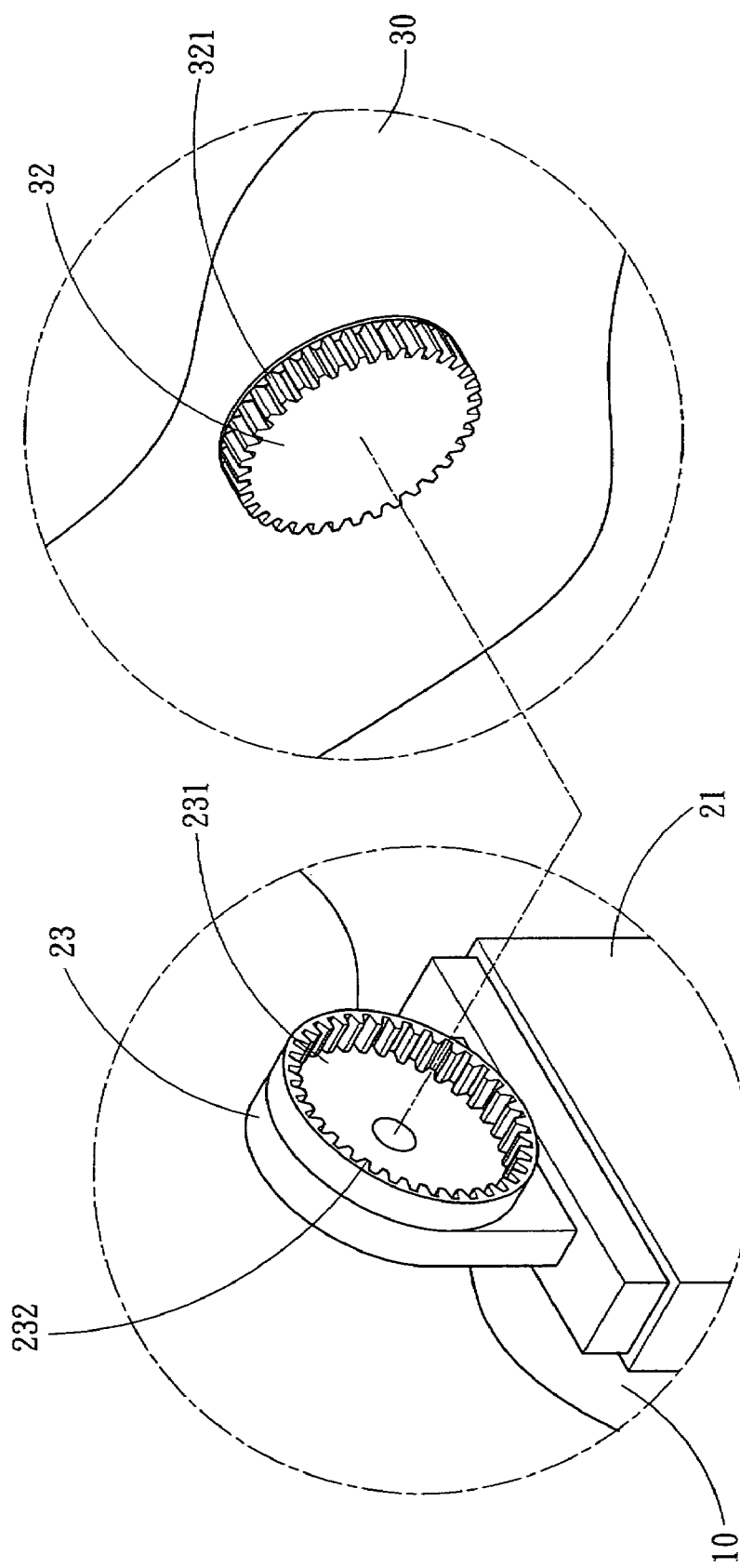
FIG. 2 is a schematic view of a partial structure of a preferred embodiment of the present invention.
Figure 3:
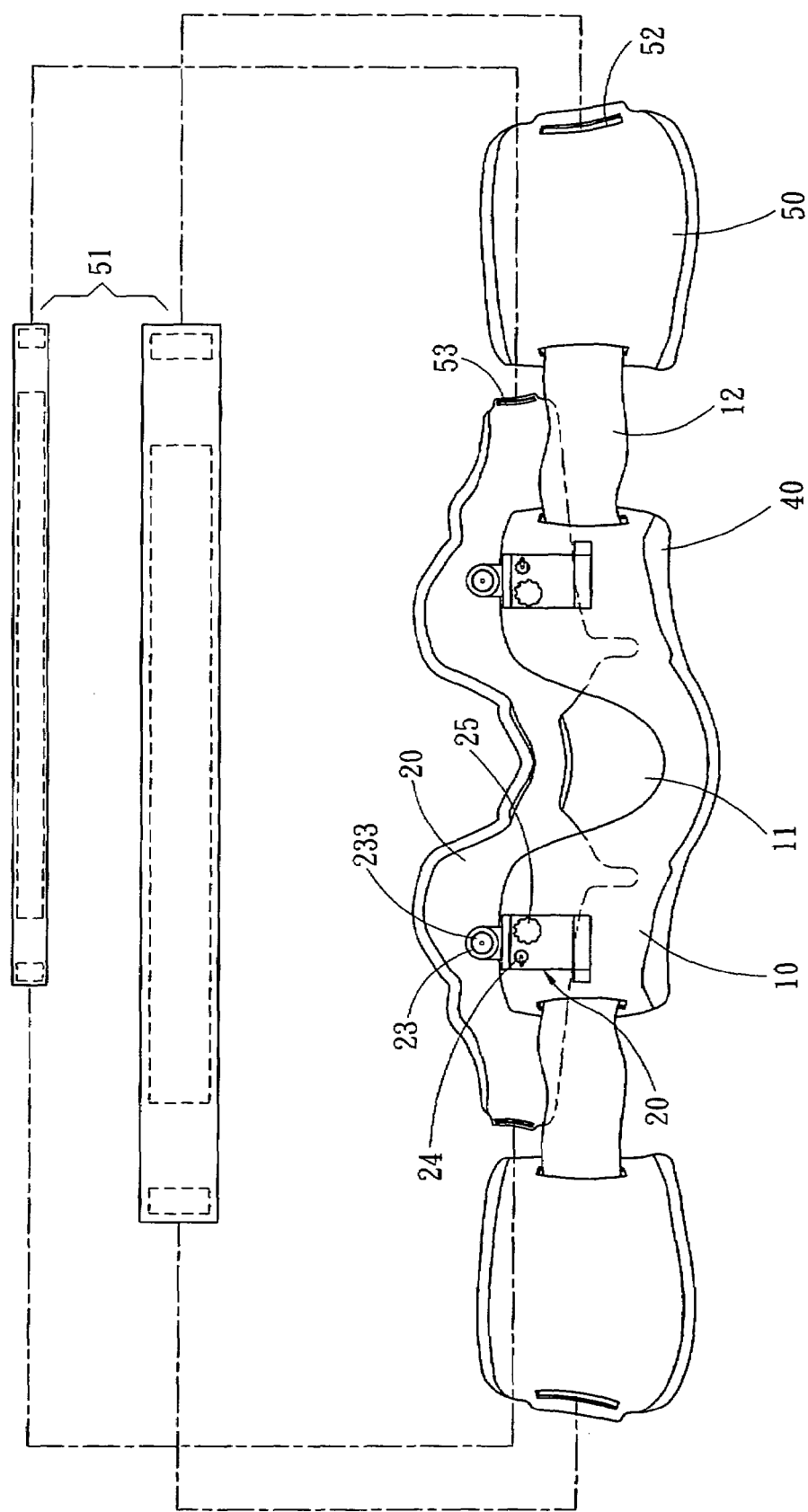
FIG. 3 is a schematic view of a structure of a preferred embodiment of the present invention.
Figure 4:
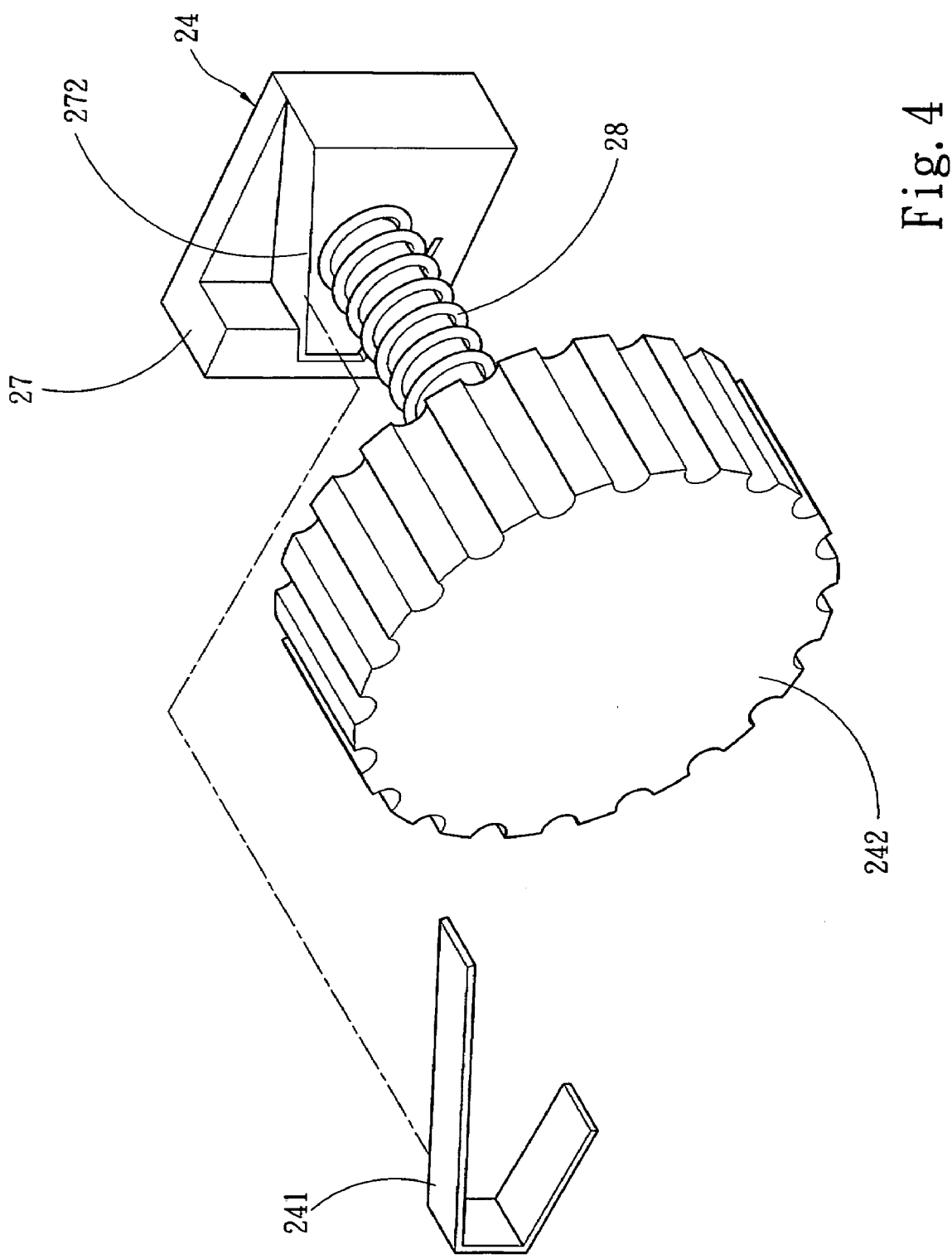
FIG. 4 is a schematic view of a limit member according to a preferred embodiment of the present invention.
Figure 5A:
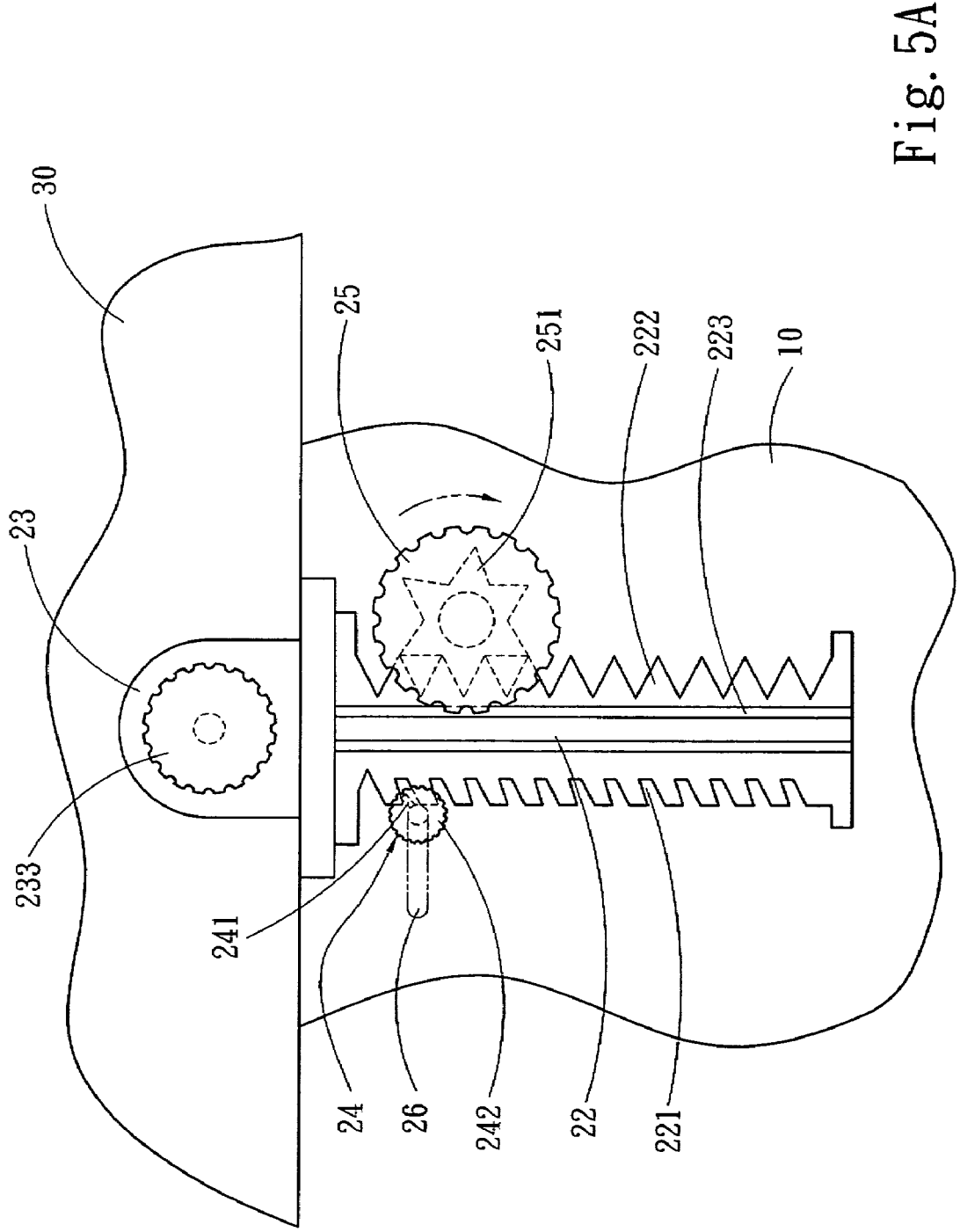
FIGS. 5A~5B are schematic views of a movement according to a preferred embodiment of the present invention.

Referring to FIGS. 1 to 3 for the schematic views of a preferred embodiment of the present invention, an adjustable neck brace of the invention is worn at a user's neck (not shown in the figure) for fixing and protecting the neck. The adjustable neck brace comprises a cover panel 10, a height adjusting plate 30 coupled to the cover panel 10, a groove 11 disposed on a surface of the cover panel 10, a supporting portion 31 protruded from the height adjusting plate 30 and corresponding to the groove 11 for supporting a user's chin. Both the cover panel 10 and the height adjusting plate 30 can be installed flexibly around the surface of the user's neck, and both sides of the cover panel 10 include a connecting plate 50 separately, and a connecting belt 12 is passed between the connecting plate 50 and the cover panel 10 to define a connecting relation. The connecting plate 50 and the height adjusting plate 30 include a through hole 52, 33 disposed separately at their respective ends for passing an adhesive latch tape 51 to adjust the internal diameter of the installation to fit the necks of different users. The internal sides of the cover panel 10 and the height adjusting plate 30 separately include a lining pad 40 (which could be made of foam) contacted with the user's body for providing a comfortable touch for users. A surface of the cover panel 10 has an adjusting device 20, and the adjusting device 20 includes a casing 21 and an adjusting rod 22 installed in the casing 21 (as shown in FIG. 5A), and an end of the adjusting rod 22 has a connecting portion 23, and an internal side of the connecting portion 23 has a containing space 231, and the height adjusting plate 30 has a connecting portion 32 contained in the containing space 231. A sidewall of the containing space 231 and an external edge of the connecting portion 32 include a plurality of gear portions 232, 321 engaged with each other, and the connecting portion 23 and the connecting portion 32 are passed by a locking member 233 to press the connecting portion 23, such that the cover panel 10 and the height adjusting plate 30 define a fixing relation, and users can adjust the locking member 233 to release such fixing relation. By changing the mutually engaged position of the gear portions 232, 321, the relative angle of the cover panel 10 and the height adjusting plate 30 can be changed to meet the requirements of different users. Both sides of the adjusting rod 22 include a plurality of positioning grooves 221 and a plurality of protrusions 222, and a surface of the casing 21 includes a limit member 24, an adjusting knob 25, and a guide track 26 corresponding to the limit member 24. The limit member 24 includes a force applying portion 242 (as shown in FIG. 4) exposed from the casing 21 and a positioning end 27 disposed in the casing 21. A surface of the positioning end 27 includes a latch groove 272 and a bracket 241 disposed at the latch groove 272 and corresponding to the latch groove 272, and the mutually symmetric bending points of the latch groove 272 and the bracket 241 define a fixing relation, and a resilient member 28 installed between the positioning end 27 and the internal wall of the casing 21 for pressing the positioning end 27, and the adjusting knob 25 is extended into the casing 21 and coupled to an adjusting gear 251 of the protrusion 222 for driving the adjusting rod 22 to ascend and descend.

Figure 5B:
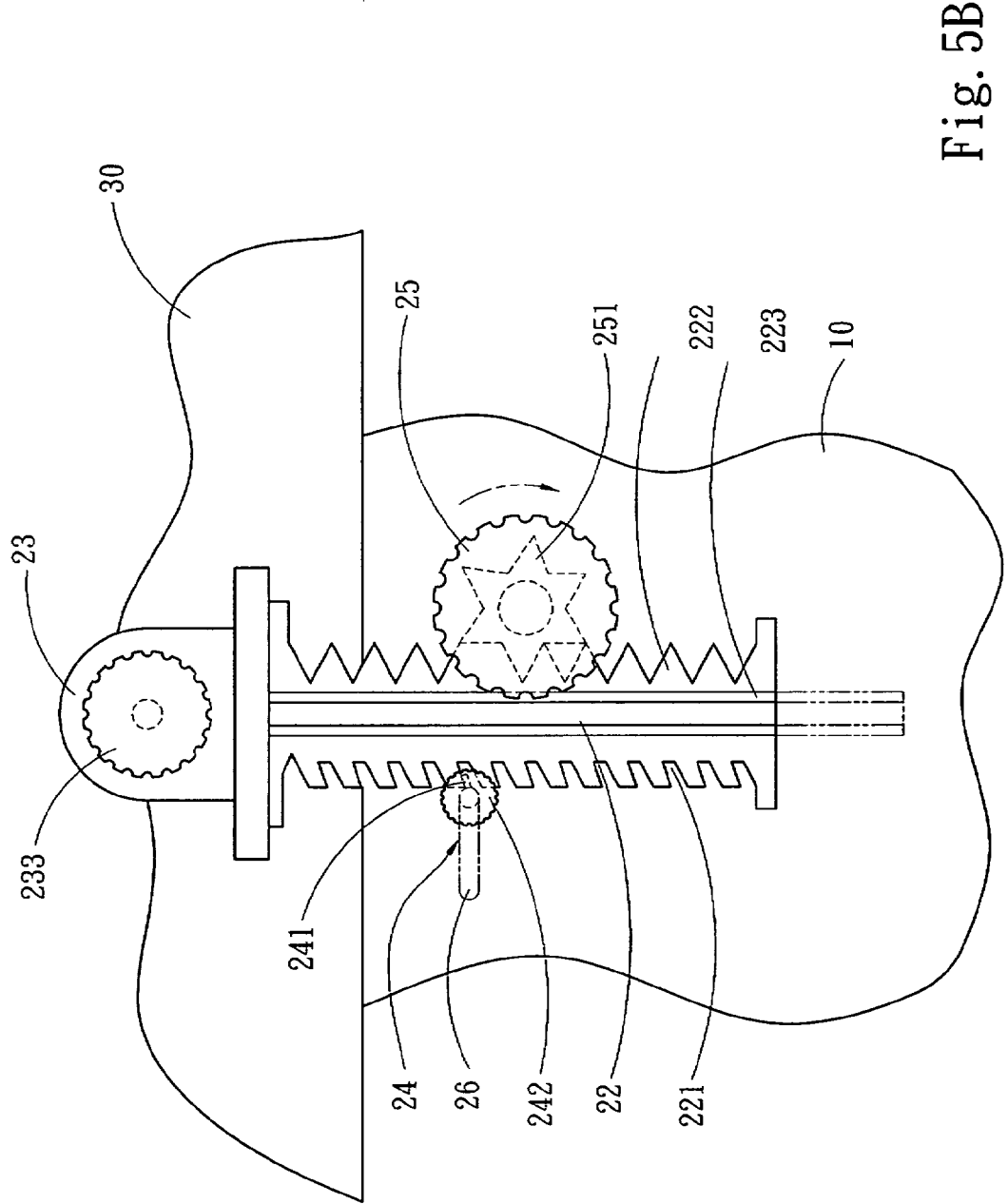
Figure 6A:
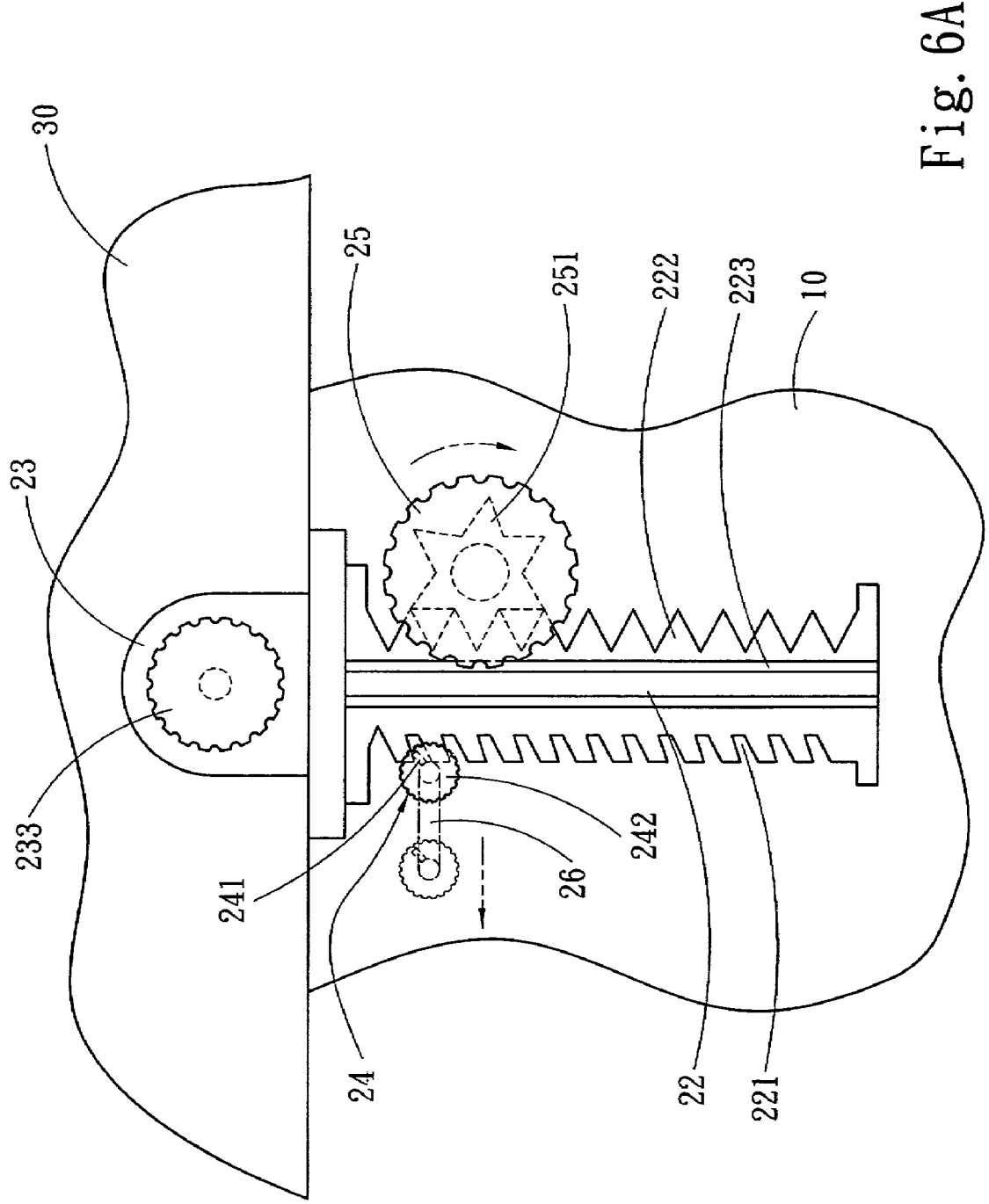
FIGS. 6A~6E are schematic views of another movement according to a preferred embodiment of the present invention.
Figure 6B:
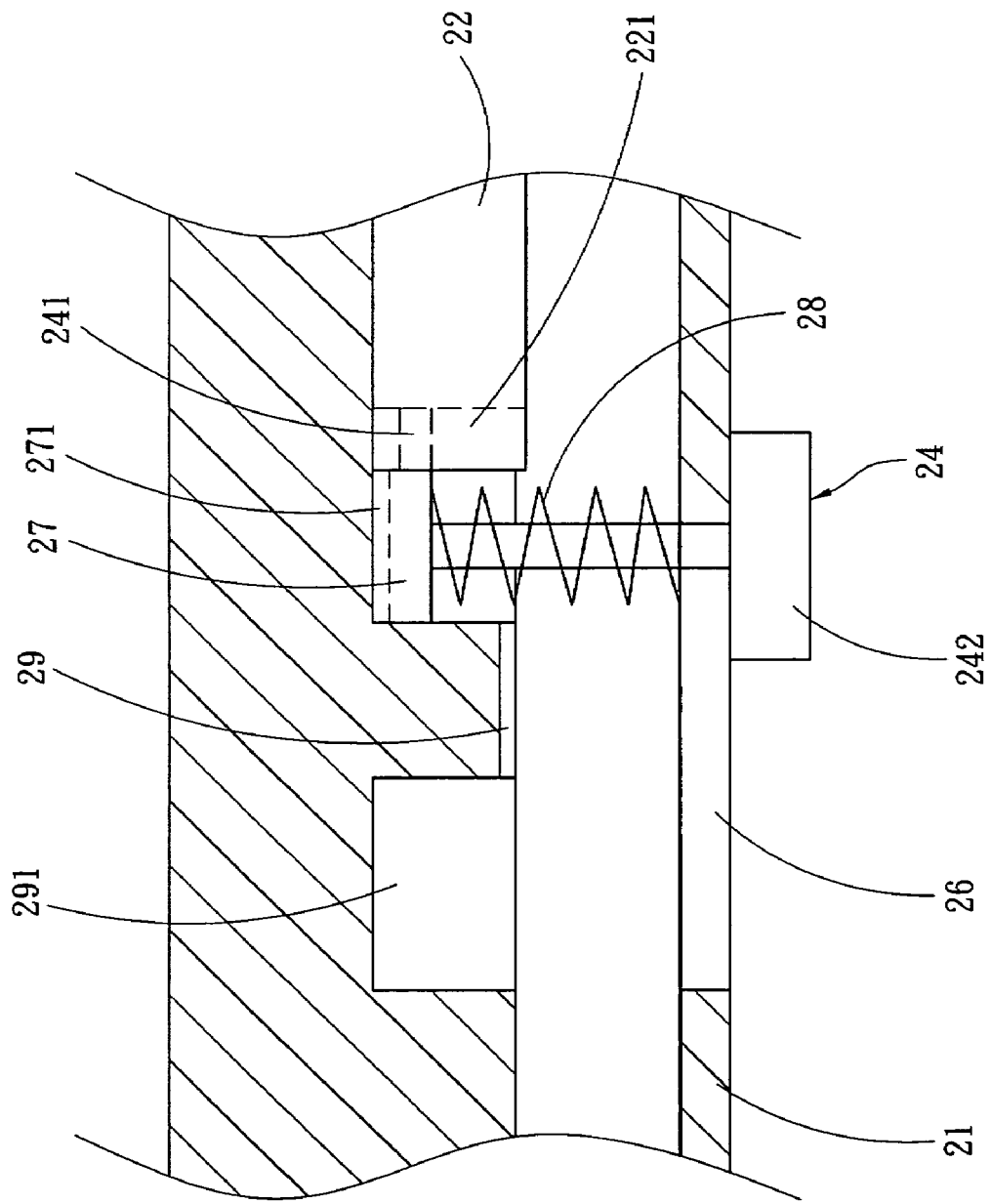
Figure 6C:
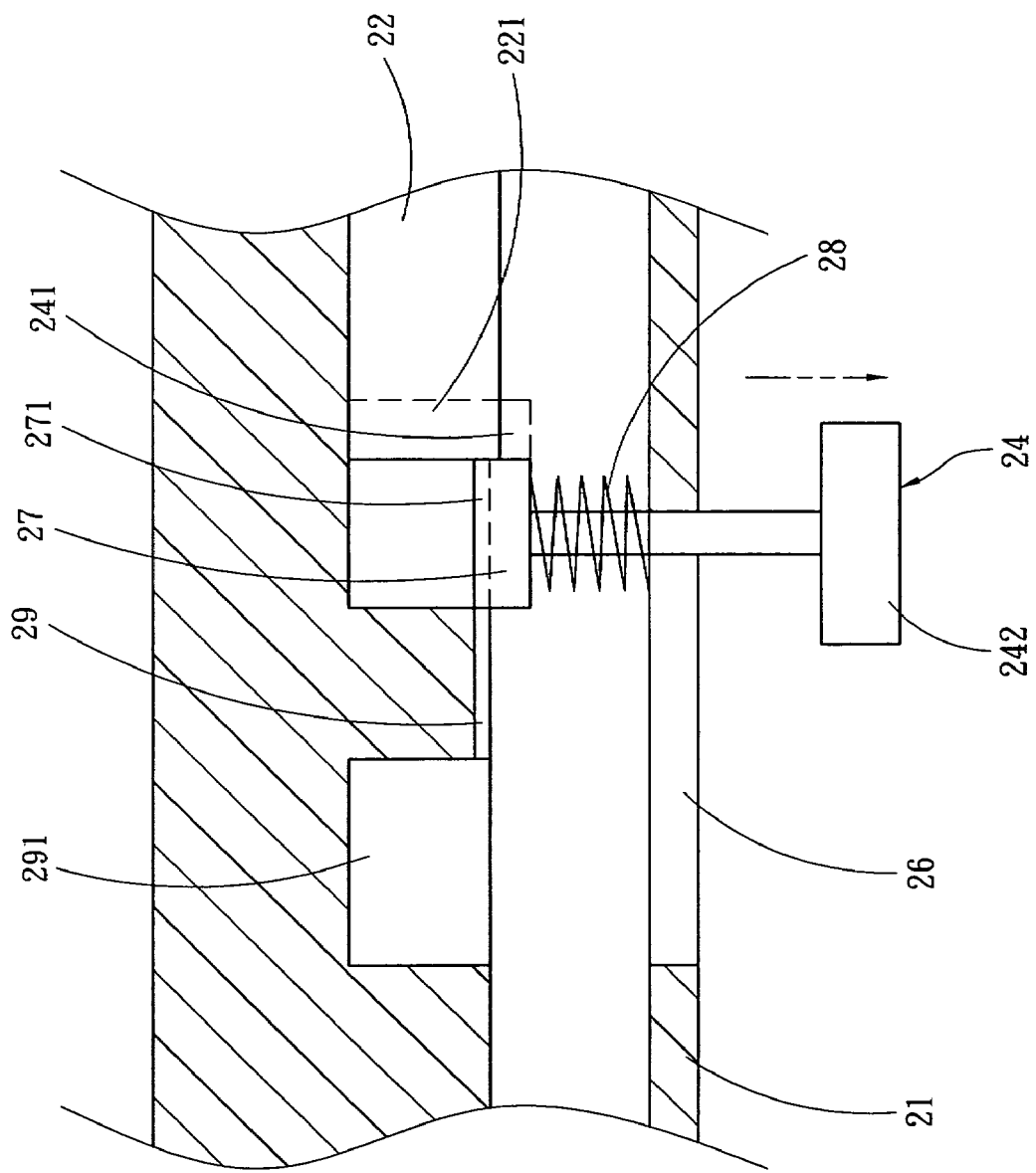
Figure 6D:
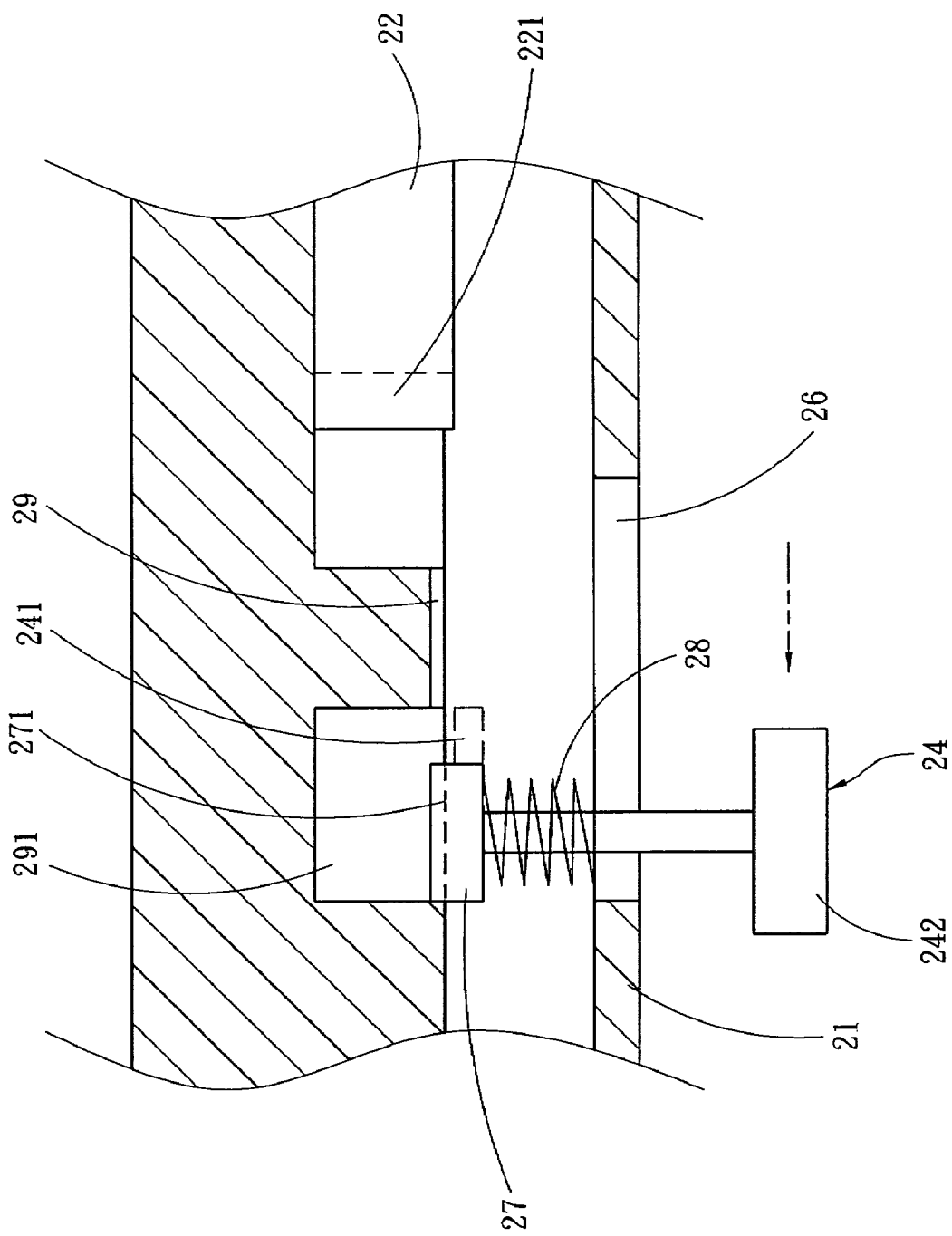
Figure 6E:
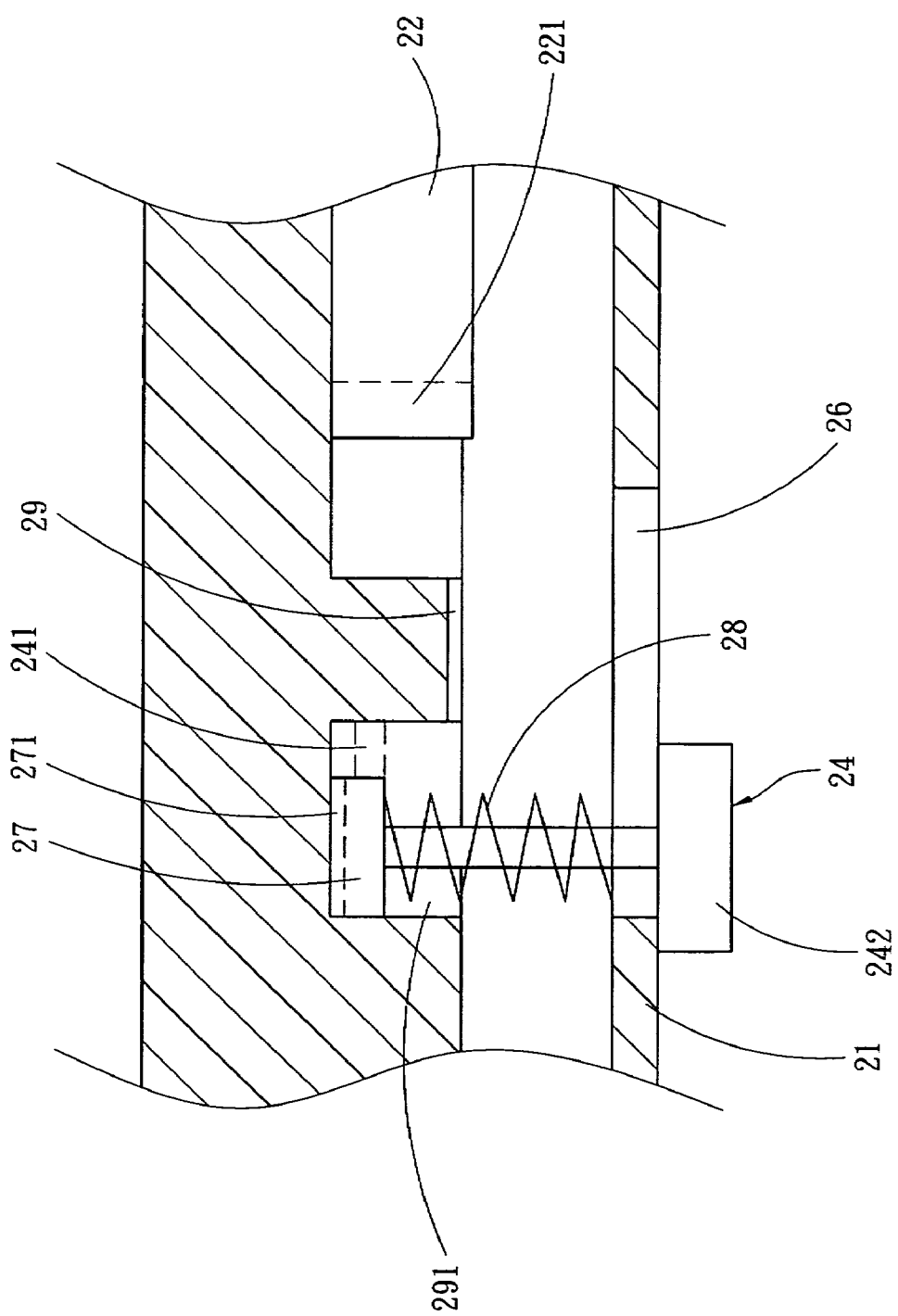

Referring to FIGS. 5A and 5B for the schematic views of the movements of a preferred embodiment of the present invention, a force is applied to the adjusting knob 25 to adjust the height of the height adjusting plate 30 and the supporting portion 31, after the user installs the cover panel 10 and the height adjusting plate 30 onto the user's neck. The adjusting knob 25 exposed from the casing 21 is turned by an external force to synchronously turn the adjusting gear 251 in the casing 21, and the adjusting gear 251 latches the protrusion 222 disposed on a side of the adjusting rod 22, so as to drive the adjusting rod 22 to produce a displacement and lift the height adjusting plate 30 and the supporting portion 31 to a desired height. In the adjusting process, the surface of the adjusting rod 22 includes two ribs 223 for stably shifting the adjusting rod 22, and the bracket 241 constantly presses the positioning groove 221 to produce a sound and a touch for providing users a feedback about a definite feel of the adjustment. After a user has adjusted the height to an appropriate height, the bracket 241 is latched into the positioning groove 221, and thus the adjusting rod 22 forms a secured fixing relation to maintain the desired height for cervical tractions and good effects of medical treatment and physical therapy.

Referring to FIGS. 6A~6E for the schematic views of another preferred embodiment of the present invention, a force is applied to a force applying portion 242 disposed on the surface of the limit member 24 to lift the limit member 24 to a desired height if a user needs to descend the height adjusting plate 30 and the supporting portion 31, so as to lift the limit member 24 accordingly. The internal wall of the casing 21 and the positioning end 27 of the limit member 24 include corresponding guide groove 29 and rib 271, such that the limit member 24 can produce a displacement along the guide track 26 on the surface of the casing 21, and the bracket 241 is separated from the positioning groove 221 to release the fixing relation. After the limit member 24 is shifted to a fixing groove 291 disposed on another side of the guide groove 29, the resilient member 28 forces the positioning end into the fixing groove 291 to provide a positioning effect. Now, users can apply a force to turn the adjusting knob 25, so that the adjusting gear 251 can be turned synchronously to drive the supporting portion 31 to descend.

In summation of the description above, the adjustable neck brace of the invention can be adjusted according to the length and diameter of a user's neck to meet the requirements of different users, so that manufacturers no longer need to produce products with various different specifications, and thus lowering the design and manufacturing costs and reducing inventory. Further, the bracket 241 of the present invention can produce a sound and a touch to provide users a feedback about the adjustment of the neck brace, in addition to giving a secured neck brace for optimizing the effects of medical treatment and physical therapy.

While the invention has been described by means of specific embodiments, numerous modifications and variations could be made thereto by those skilled in the art without departing from the scope and spirit of the invention set forth in the claims.

What is claimed is:

1. An adjustable neck brace, which is worn at a user's neck for fixing a cervical vertebra, comprising:
   a cover panel;
   an adjusting device, installed on a surface of said cover panel and having a casing, an adjusting rod installed in said casing, a connecting portion disposed at an end of said adjusting rod and exposed from said casing, a plurality of positioning grooves and a plurality of protrusions disposed separately on both sides of said adjusting rod, a limit member and an adjusting knob both disposed on the surface of said casing, a bracket disposed on said limit member and corresponding to said positioning groove, and an adjusting gear extended from said adjusting knob and coupled to said protrusion; and
   a height adjusting plate, coupled to said connecting portion and having a supporting portion protruded from said height adjusting plate for supporting a user's chin, and said adjusting knob being turned and said adjusting gear driving said adjusting rod to produce a displacement to lift said supporting portion to a desired height, and said bracket being latched into said positioning groove to define a fixing relation.

2. The adjustable neck brace of claim 1, wherein said casing includes a guide track disposed on a surface of said casing corresponding to said limit member, and said limit member includes a force applying portion disposed thereon.

3. The adjustable neck brace of claim 2, wherein said force applying portion links said limit member to ascend by a force and displace along said guide track, such that said bracket is separated from said positioning groove to release said fixing relation.

4. The adjustable neck brace of claim 1, wherein said limit member includes a positioning end for connecting said bracket and said positioning end includes a resilient member disposed on an internal wall of said casing for pressing said positioning end.

5. The adjustable neck brace of claim 4, wherein said positioning end includes a latch groove disposed on a surface of said positioning end for installing said bracket, and said latch groove and said bracket have corresponding symmetric bending points to define a fixing relation.

6. The adjustable neck brace of claim 1, wherein said connecting portion includes a containing space disposed on an internal side of said connecting portion, and said height adjusting plate includes a connecting portion contained into said containing space.

7. The adjustable neck brace of claim 6, wherein a sidewall of said containing space and an external edge of said connecting portion include a plurality of gear portions engaged with each other.

8. The adjustable neck brace of claim 6, wherein said connecting portion includes a locking member passing through said connecting portion for pressing against said connecting portion, such that said cover panel and said height adjusting plate define a fixing relation.

9. The adjustable neck brace of claim 8, wherein said locking member can be turned to release the fixing relation, and the position of engaging said gear portion is altered to change the angle of said cover panel with respect to said height adjusting plate.

10. The adjustable neck brace of claim 1, wherein said cover panel includes a connecting plate disposed on both sides of said cover panel separately, and a connecting belt is installed between said connecting plate and said cover panel for defining a connecting relation, and said connecting plate and said height adjusting plate include a through hole disposed at their respective ends for passing an adhesive latch tape.

* * * * *